(12) United States Patent
Kureshy et al.

(10) Patent No.: US 7,354,389 B2
(45) Date of Patent: Apr. 8, 2008

(54) MICROARRAY DETECTOR AND METHODS

(75) Inventors: Fareed Kureshy, Del Mar, CA (US);
Vijay K. Mahant, Murrieta, CA (US);
Shailendra Singh, Carlsbad, CA (US);
Xiaohua Shen, San Jose, CA (US)

(73) Assignee: Autogenomics, Inc., Carlsbad, CA (US)

( * ) Notice: Subject to any disclaimer, the term of this patent is extended or adjusted under 35 U.S.C. 154(b) by 402 days.

(21) Appl. No.: 10/509,985

(22) PCT Filed: May 28, 2003

(86) PCT No.: PCT/US03/17073

§ 371 (c)(1),
(2), (4) Date: Nov. 16, 2004

(87) PCT Pub. No.: WO03/100474

PCT Pub. Date: Dec. 4, 2003

(65) Prior Publication Data

US 2005/0118640 A1    Jun. 2, 2005

Related U.S. Application Data

(60) Provisional application No. 60/383,896, filed on May 28, 2002.

(51) Int. Cl.
*C40B 60/08*    (2006.01)

(52) U.S. Cl. ............................................. 506/37; 435/6
(58) Field of Classification Search .................... None
See application file for complete search history.

(56) References Cited

U.S. PATENT DOCUMENTS 6,471,916 B1 *  10/2002  Noblett ..................... 422/82.08

FOREIGN PATENT DOCUMENTS

GB    WO 00/43819    *  7/2000

* cited by examiner

*Primary Examiner*—Jon D. Epperson
*Assistant Examiner*—Jeffrey S. Lundgren
(74) *Attorney, Agent, or Firm*—Fish & Associates, PC

(57) ABSTRACT

A detector for optical analysis of a biochip determines the focal position of a plurality of analytes on the biochip using one or more registration markers on the biochip, wherein the analytes and the registration marker are illuminated by different light sources. Therefore, contemplated configurations will significantly reduce overall focusing time and automate proper positioning of the biochip, while allowing to determine a focal position without photobleaching or other undesirable effects on optically labile compounds. Thus, automated analyses can be performed without manual user intervention.

13 Claims, 3 Drawing Sheets

MICROARRAY DETECTOR AND METHODS

This application claims the benefit of U.S. provisional patent application with the Ser. No. 60/383,896, filed May 28, 2002, and international patent application with the Ser. No. PCT/US02/17006, filed May 29, 2002, both of which are incorporated herein by reference.

FIELD OF THE INVENTION

The field of the invention is optical detection, and especially as it relates to signal detection from an array with bound analytes.

BACKGROUND OF THE INVENTION

With the advent of high-throughput screening of small-molecule, nucleic acid, and polypeptide arrays, new challenges have arisen to provide accurate and fast data acquisition. Depending on the type of array, numerous configurations and methods for data acquisition are known in the art.

For example, arrays can be electronically queried to detect hybridization of a nucleic acid sample to an immobilized probe of a probe array, typically allowing an operator to obtain a relatively high number of data in relatively short time. While such systems are advantageous in various respects, several difficulties remain. For example, the quantification range for determination of hybridized molecules is at least in some circumstances less than desirable. Furthermore, if molecules other than nucleic acids need to be determined electronic detection may not be available or technically feasible. Still further, electronic detection is relatively expensive and poses at least some difficulties where a user wants to customize an array.

To circumvent at least some of the disadvantages associated with electronic detection, arrays may be optically queried to detect binding of an analyte to an immobilized probe of a probe array. Most commonly, such arrays have a generally flat surface and optical detection is performed With a scanner analyzing emitted and/or absorbed light from a label that is bound to the analyte. In one typical example, a scanner for such arrays (typically disposed on a microscope slide) may illuminate the array using narrowband excitation (e.g., using a laser), while a photo-multiplier tube (PMT) is used as detector. Narrow band excitation is particularly advantageous since a higher quantum density is achieved at the label, which will generally result in a higher resolution acquisition. Alternatively, the array may be illuminated using wideband excitation (e.g., Xenon light) and a charge coupled device (CCD) detector is employed to detect the signal from the label. Among other advantages, wideband excitation is particularly advantageous where multiple labels are detected using the same scanner.

However, regardless of the particular excitation-type, numerous problems associated with scanner-based detection remain. Most significantly, the illuminated array is frequently not positioned at the same distance relative to the detector (e.g., the array is warped, or has a surface unevenness), typically resulting in inaccurate detection of the signal. Conceptually, such inaccuracies could be resolved by providing a focusing mechanism to the scanner. However, such focusing mechanism would likely significantly reduce the speed at which the scanner would acquire data. Moreover, by exposing non-analyzed analytes to illumination conditions for prolonged periods of time, photobleaching of the labels will most likely result in inaccuracies of the later obtained test results.

To compensate for surface unevenness, spot-by-spot illumination with spot-by-spot analysis can be performed as described in U.S. Pat. No. 6,471,916. Such systems further advantageously allow calibration of signal strength using calibration points on the array. However, while such systems typically provide relatively accurate data, the time required for focusing the detection optics on a spot-by-spot basis increases with increasing array size. Thus, even with relatively small arrays (e.g., 50 to 100 probes), detection time tends to become unacceptable, especially where high-throughput screening is desired.

Thus, although various systems for optical detection of signals from microarrays are known in the art, numerous problems still remain. Therefore, there is still a need for improved configurations for optical microarray detectors.

SUMMARY OF THE INVENTION

The present invention is directed to an analytic system for detection of a plurality of analytes that are bound to a biochip, wherein an optical detector uses registration markers illuminated by a first light source to determine a focal position for detection of the analytes that are illuminated by a second light source.

In one aspect of the inventive subject matter, the analytic system includes a platform that is coupled to a detector and movable along an x-coordinate, a y-coordinate, and a z-coordinate relative to the detector (in response to a registration marker signal), wherein the platform is configured to receive a biochip, wherein the biochip has a registration marker and further has a plurality of analytes in predetermined positions relative to the registration marker. A first light source illuminates the registration marker to generate a registration marker signal, and a second light source illuminates at least one of the analytes to generate an analyte signal, wherein the focal position for detection of the analyte signal by the detector is determined by the analytic system using the registration marker signal.

It is especially preferred that the first light source has a wavelength maximum that is different from an absorption maximum of an optically detectable label of the at least one of the plurality of analytes, and suitable systems may further include a third light source that illuminates the same or different analyte to generate a second analyte signal, wherein the third light source has a wavelength maximum that is different from both, the wavelength maximum of the first light source and the absorption maximum of the optically detectable label the analyte.

Additionally, or optionally, the registration marker and analyte may be illuminated at different angles by the first and the second light source, respectively. It is further preferred that the first light source is a laser or a light emitting diode, while the second light source is a laser. With respect to the registration marker, fluorescent dyes, luminescent compounds, phosphorescent compounds, and/or reflective compounds are generally preferred. Similarly, the analyte signal is preferably a fluorescence signal, a chemiluminescence signal, and/or a phosphorescence signal. Particularly preferred detectors include a photo-multiplier tube or a charge-coupled device, which may be optically coupled to a confocal microscope or a dark field microscope.

Furthermore, where desirable, it is contemplated that the biochip may include a second and a third registration marker, wherein the focal position for detection of the analyte signal by the detector is determined by the analytic system using registration marker signals from all of the registration markers, and optionally, that the analyte signal is normalized by the analytic system using a positive control marker on the biochip. Particularly preferred biochips will also include a housing that is at least partially transparent for light emitted from the first light source, wherein the registration marker is illuminated at least in part through the housing. Especially preferred analytic systems further include a data transfer interface that is electronically coupled to the detector, wherein the data transfer interface provides data to a computer in a remote location (or location where the analytic system is located).

In another aspect of the inventive subject matter, contemplated analytic systems for micro-optical analysis of a biochip having a first light source and a second light source, wherein the first light source illuminates a registration marker on the biochip to provide a registration marker signal, wherein the second light source illuminates an analyte to provide an analyte signal, and wherein a focal position for detection of the analyte signal with a confocal microscope is determined using the registration marker signal. The analyte signal in such systems typically has a substantially round shape with a diameter of no more than 500 micrometer (and more typically no more than 200 micrometer), and a test result is calculated from an average or integrated signal value of a portion of the round shape. Alternatively, the test result can be calculated from the total fluorescence emanating from the illuminated area.

Further contemplated systems may include a third light source that illuminates the analyte to generate a second analyte signal, and it is generally preferred that the first light source is a laser or a light emitting diode, and that the second light source is a laser. In further preferred aspects, the registration marker and the analyte are illuminated at a different angle by the first and the second light source, respectively.

Various objects, features, aspects and advantages of the present invention will become more apparent from the following detailed description of preferred embodiments of the invention, along with the accompanying drawing.

DETAILED DESCRIPTION

Figure 1:
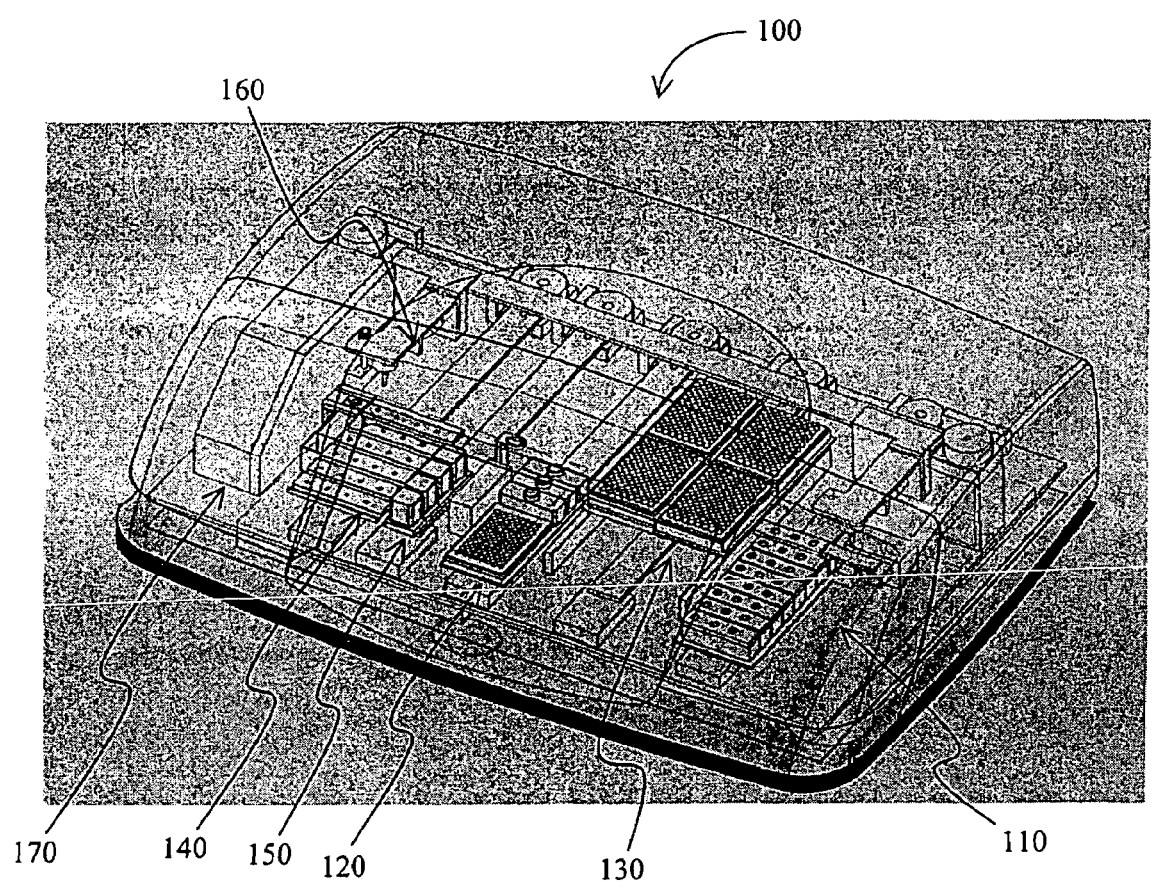
FIG. 1 is a schematic view of an exemplary analytic device according to the inventive subject matter.

As used herein, the term "biochip" generally refers to a carrier that has a plurality of probes (to which an analyte may be coupled) in predetermined positions. In especially preferred biochips, at least one of the probes is coupled to the carrier via a crosslinker that is disposed in a matrix, and exemplary multi-substrate chips are described in commonly-owned and copending U.S. patent application Ser. No. 10/346,879, filed Jan. 17, 2003, and the PCT applications with the Ser. Nos. PCT/US02/03917, filed Jan. 24, 2002, and PCT/US01/47991, filed Dec. 11, 2001, all of which are incorporated by reference herein.

The term "predetermined position" of an analyte refers to a particular position of the analyte on the chip that is addressable by at least two coordinates relative to a registration marker on the chip, and particularly excludes a substantially complete coating of the chip with the analyte an/or probe. Therefore, preferred pluralities of predetermined positions will include an array with a multiple rows of substrates forming multiple columns. As further used herein the term "registration marker" refers to a marker on the biochip that is used to provide a reference point for a position of an analyte. In especially preferred aspects, the registration marker is optically detectable and comprises a fluorescent dye, a luminescent, light-absorbing, and/or light-reflective compound, wherein illumination of the registration marker is most preferably performed at a wavelength that is not absorbed by the label of the analyte.

As further used herein, the term "probe" generally refers to any molecule, complex of molecules, or cell that binds to an analyte with a dissociation constant $K_D \leq 10^{-2}M$, and more typically $K_D \leq 10^{-3}M$, at a temperature of 25° C. and physiological buffer conditions (e.g., pH between 6.5 and 8.5, and ionic strength sufficient to maintain native conformation, viability, and/or Watson-Crick hybridization (between ligand and anti-ligand) of the anti-ligand). Thus, suitable probes include nucleic acids (and their analogs), polypeptides, lipids, macromolecular complexes of nucleic acids, polypeptides, carbohydrates, and lipids, as well as viruses, bacteria and/or eukaryotic cells. In further preferred aspects, it should also be appreciated that the probe may further include a label. For example, where a probe on the biochip may include a fluorescent label, wherein the fluorescence is quenched by a molecule that binds to the probe. Alternatively, a probe may also include a label for calibration of a signal in a quantitative assay.

Similarly, the term "analyte" as used herein refers to any molecule, complex of molecules, or cell that binds to the probe with a dissociation constant of $K_D \leq 10^{-2}M$ and more typically $K_D \leq 10^{-3}M$, at a temperature of 25° C. and physiological buffer conditions (i.e., pH between 6.5 and 8.5, and ionic strength sufficient to maintain native conformation, viability, and/or Watson-Crick hybridization (between ligand and anti-ligand) of the anti-ligand). Therefore, suitable analytes include nucleic acids (and their analogs), polypeptides, lipids, metabolites, hormones, macromolecular complexes of nucleic acids, polypeptides, carbohydrates, and lipids, as well as viruses, bacteria and/or eukaryotic cells. Still further, it should be understood that the analyte may include an optically detectable label, which may be naturally present in the analyte, or coupled to the analyte before, during or after binding of the analyte to the probe. Particularly contemplated labels include light-absorbing compounds, fluorescent labels, phosphorescent labels, and luminescent labels that produce an analyte signal where the label is coupled to the analyte. Contemplated analyte signals therefore include a fluorescence signal, a chemiluminescence signal, or a phosphorescence signal. Thus, it should be recognized that a probe and an analyte form a optically detectable binding pair, wherein the analyte is optically detected via the label.

As still further used herein the term "focal position" refers to (1) a position of the biochip relative to the detector in which an image of the analyte and/or label produced by the detector has a maximum clear outline and/or maximum sharp detail, and/or (2) a position of the biochip in the detector in which a predetermined movement of the biochip along the x-coordinate and/or y-coordinate will place the biochip into a new position consistent with detection of a signal from a labeled analyte/probe. Thus, it should be recognized that the focal position of a biochip may be adjusted by translating the biochip along the z-coordinate (i.e., by moving the biochip up or down) to maximize sharpness and detail, and/or by translating the biochip along the x-coordinate/y-coordinate (i.e., by moving the biochip left or right and/or forward or backward) to properly position the biochip relative to the light beam that irradiates the labeled analyte/probe (e.g., where the light beam has a diameter of about 80 micrometer and the labeled analyte/probe spot has a diameter of about 100 micrometer, the chip is positioned such that the light beam centrally irradiates the labeled analyte/probe).

The inventors discovered that optical detection of various analytes may be performed in an analytic system by determination of the focal position for a plurality of analytes using a registration marker that is illuminated with a light source having a wavelength that substantially not absorbed (i.e., less than 20%, more typically less than 10%) by a label coupled to the analyte. Such systems not only significantly reduce the overall time required for accurate data acquisition for the plurality of analytes, but also avoid heretofore frequently experienced photobleaching of the label while adjusting a biochip to the correct focal position.

In one particularly preferred exemplary configuration as shown in FIG. 1, an analytic system 100 has an automated reagent station 110, a sample station 120, a pipette tip station 130, a stringency area 140 with biochip magazines 150, an automated pipette/manipulator 160, and an optical detection station 170. A more detailed schematic view of the optical detection station 170 is provided in FIG. 2, in which system 200 includes a confocal microscope 210 that is optically coupled to a detector 220. Platform 230 receives and retains biochip 240 which has a registration marker 242 and a plurality of probes/analytes 244 in predetermined positions.

A first light source 250 (preferentially circumferentially arranged above the biochip 240) illuminates the entire biochip (and more preferably even the entire platform) at a first angle relative to the surface of the platform 230 as schematically depicted by the wide arrows. Registration marker 242 emits/reflects light in response to the illumination by the first light source as schematically indicated by the dotted line, and the emitted and/or reflected light is detected by the detector 220. More typically, however, biochip 240 will include at least a second and/or a third registration marker (not shown). Computer 260 executes an autofocus loop to determine the focal position of the biochip based on the emitted and/or reflected light signal(s) from the registration marker(s). computer 260 also determines the absolute position of the registration marker 242 relative to the detector 220.

Once the focal and absolute position of the registration marker(s) is determined, the computer then calculates the proper position (i.e., focal position, and x and y coordinate relative to the registration marker) of the first probe/analyte based on the previously determined position of the registration marker and based on the known spatial relationship between the registration marker and the plurality of analytes/probes. For optical analysis of the analytes, the computer 260 then drives the x,y,z-actuators of control unit 232 to position the biochip relative to the confocal microscope in a position consistent with the predetermined focal position for and position of the analyte(s)/probe(s).

The biochip is then illuminated with a focused laser beam from the second light source 270 (via a dichroic mirror) as schematically indicated by the slender arrow such that only one analyte 244 at the time is illuminated by the second light source. Light emitted and/or reflected from the analyte 244 as schematically indicated by the dotted arrow then passes through the dichroic mirror and is detected and quantified by the detector 220 and computer 260. Where desirable, the same analyte 244 may be simultaneously or sequentially illuminated by a third light source 272 to provide a second analyte signal. Data transfer interface 262 may communicate operational and/or test related data to a computer outside of the analytic device (which may be operated by the same operator than the analytic device, or which may be in a remote location relative to the analytic device).

With respect to the detector, it is generally contemplated that all known detectors are suitable for use herein so long as such detectors can provide a digital and/or analog video signal to a computer. Therefore, and especially depending on the particular nature of the first and second light sources, but also on the emission/reflection strength of the registration marker and analyte, suitable detectors will particularly include a CCD chip (e.g., where emitted/reflected light intensity is relatively high) or a PMT detector (typically, where emitted/reflected light intensity is relatively high). However, alternative detectors are also contemplated suitable for use herein, and exemplary alternatives and further discussion on image detection are provided elsewhere (L. J. van Vliet, F. R. Boddeke, D. Sudar, and I. T. Young, Image Detectors for Digital Image Microscopy, in: M. H. F. Wilkinson, F. Schut (eds.), Digital Image Analysis of Microbes; Imaging, Morphometry, Fluorometry and Motility Techniques and Applications, Modern Microbiological Methods, John Wiley & Sons, Chichester (UK), 1998, 37-64, incorporated by reference herein).

Similarly, it should be recognized that the nature and exact configuration of the confocal microscope may vary considerably, and it is generally contemplated that all magnification devices suitable for detection and quantification of a single analyte with a maximum length and/or width of 1000 micrometers are deemed appropriate for use in conjunction with the teachings presented herein. Therefore, alternative magnification devices include bright-field and dark-field microscopes, as well as trans- and/or epifluorescence microscopes. However, and regardless of the nature of the particular magnification device, it is contemplated that the detector is optically coupled to the magnification device to provide an image of the biochip, the registration marker, and/or the analyte/sample. Optic coupling is typically directly, for example, using a common conduit between the magnification device and the detector. Alternatively, indirect coupling may also be employed. For example, where the analyte signal is relatively weak, an intensifier screen may be interposed between the magnification device and the detector.

It an especially preferred aspect of the inventive subject matter, the first light source comprises one, and more typically several light emitting diodes that are arranged such that the light of the diodes illuminate the entire biochip, and most preferably the entire platform. Use of light emitting diodes (LEDs) for the first slight source is particularly advantageous from various aspects. Among other things, LEDs (and especially red LEDs) provide a significantly less intense light and will therefore be less likely to interfere with light sensitive analytes, probes, and/or labels on the analyte. Moreover, LEDs may be chosen such that the light emitted has a wavelength maximum that is different (and most preferably lower) than an light absorption maximum of the analyte and/or label. Consequently, it should be especially recognized that the first light source will provide sufficient light to determine a proper focal position for the analytes/probes without significant photobleaching (or other undesirable photodestructive effect) to a label that is coupled to the probe and/or analyte.

Alternatively, a laser may be used as a first light source to illuminate the registration marker, and with respect to the wavelength and intensity, the same considerations as provided above for the LEDs apply. Furthermore, while not specifically preferred, a polychromatic light source (e.g., incandescent or fluorescent light source) may also be employed. In such systems, it is generally preferred however that the light provided by the first light source is filtered such that interference (e.g., absorption, photobleaching, etc) with the label(s) on the biochip is minimized, or even eliminated. Where a laser is employed as first light source, it is generally preferred that the laser beam is collimated by a lens or other optical system to provide illumination of the entire biochip or even entire platform. Thus, it should be appreciated that the light from the first light source may be directly provided to the registration marker, biochip, and/or platform, or indirectly via a lens, filter, or other optical system.

Similarly, with respect to the second light source, it is generally preferred that the second light source comprises a laser, preferably with a wavelength this is shorter than the wavelength of the first light source, and even more preferably with a wavelength that substantially matches (i.e., laser emission within +/−30 nm, more typically +/−15 nm of absorption maximum) that absorption of a fluorogenic (e.g., Cy3, Cy5, or Cy7) and/or luminogenic compound. For example, particularly suitable second light sources include a Nd:YAG laser with a wavelength maximum of about 532 nm, and a diode laser with a wavelength maximum of about 635 nm, which will preferably have a power of between about 0.1 mW and 50 mW. There are numerous lasers known in the art, and all such lasers are considered suitable for use herein. Likewise, the same considerations apply for an optional third light source, wherein it is generally preferred that the wavelength maximum of the third light source is different, and more preferably lower than the wavelength maximum of the second light source.

Still further, the inventors also contemplate that the second and/or third light source may also be a polychromatic light source (e.g., incandescent or fluorescent light source). As discussed above, it is then generally preferred that the light provided by the first light source is filtered such that interference (e.g., absorption, photobleaching, etc) with the label(s) on the biochip is minimized, or even eliminated. Thus, it should be appreciated that the light from the second and/or third light source may be directly provided to the analyte/probe, biochip, and/or platform, or indirectly via a lens, filter, or other optical system.

Figure 2:
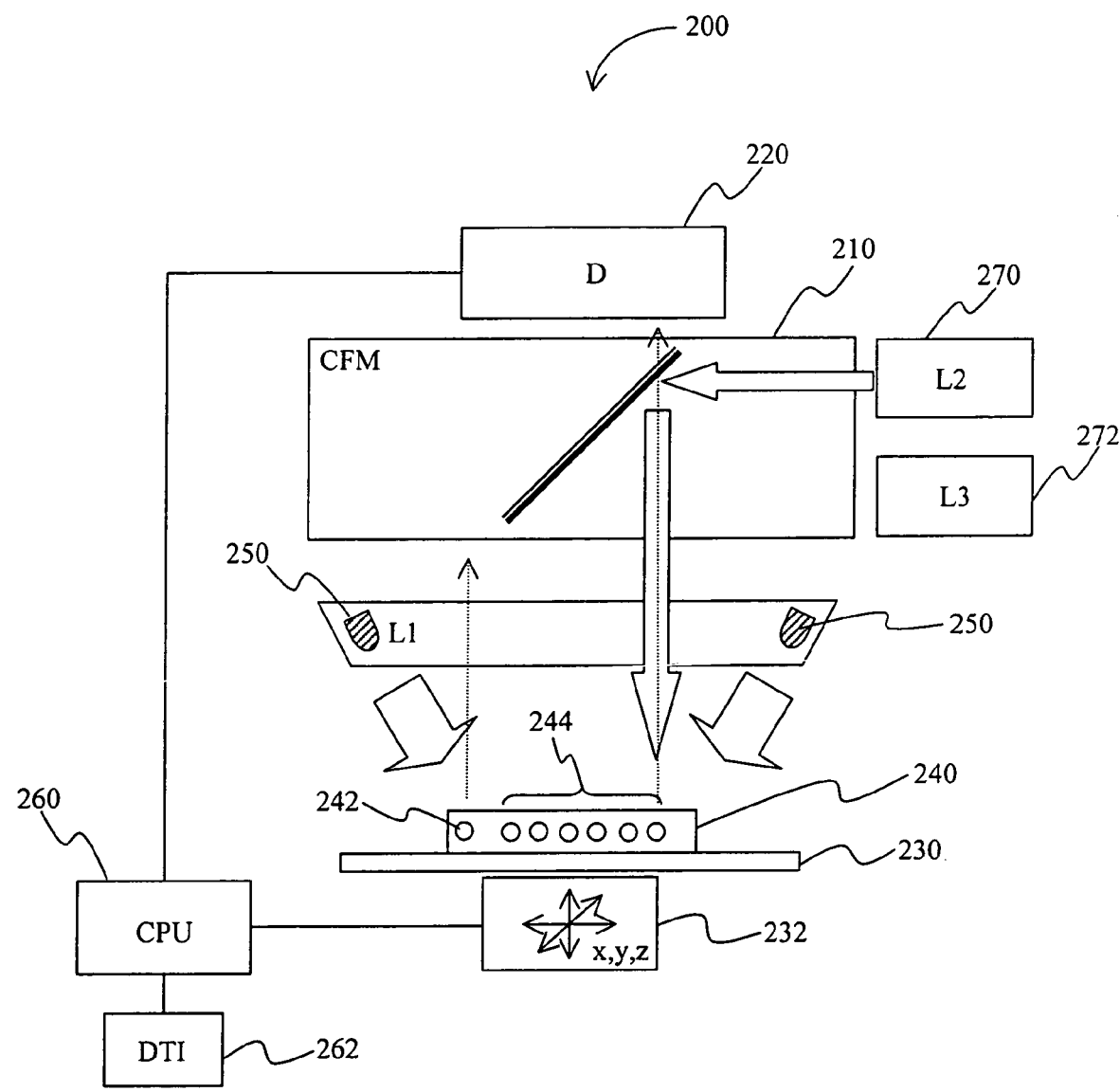
FIG. 2 is a schematic view of one exemplary detector configuration according to the inventive subject matter.

Regardless of the type of second and/or third light source, it is generally preferred that the light beam from the second and/or third light source is focused such that the beam illuminates only one probe spot (i.e., area where a probe is deposited on the biochip) or analyte spot (i.e., area where an analyte, typically coupled to an optically detectable label, is bound to a probe spot) at the time. Illumination of a probe/analyte spot may be incomplete (e.g., only one side of the probe/analyte spot is illuminated, or only the center portion of a probe/analyte spot is illuminated) or complete (illumination area identical with, or larger than the probe/analyte spot). In further preferred aspects, illumination may also be performed using the second and third light source at the same time. Such illumination may be particularly advantageous where the probe includes a reference label and the analyte includes a second, distinct label to provide normalization of the test result. Thus, in yet another preferred aspect of the inventive subject matter, it should be recognized that the registration marker and the probe, analyte, and/or label are illuminated at a different angle by the first and the second light source, respectively. For example, where dark field illumination of the reference marker is particularly desirable, the reference marker may be illuminated through the housing. Alternatively, the registration marker (as depicted in FIG. 2) may also be illuminated at an angle of between about 10 and 45 degrees (relative to the light path of the first light source).

With respect to the platform, it should be recognized that in preferred aspects of the inventive subject matter the platform is functionally coupled to a stringency area in a manner such that the biochip can be automatically moved (i.e., without manual intervention of an operator) from the stringency area to the detector platform by an actuator. Consequently, it should be especially appreciated that analytic devices according to the inventive subject matter allow automatic transfer from a fluidics area to a detection area. In one especially preferred example, the stringency area is adjacent to a magazine in which biochips are stored. An actuator will then automatically transfer the biochip onto the stringency area, where reagents and sample is added to the biochip. Temperature control and further liquid management are then performed on the stringency area (e.g., rinsing with buffer, incubation at preset temperature, etc.), and when the biochip is ready for analysis, the actuator will then move (typically push) the biochip from the stringency area to the detector platform. While not limiting to the inventive subject matter, it is generally preferred that the detector platform includes a guiding element for a biochip (e.g., rail, depression, notch, etc.) to ensure repeated and consistent positioning of the biochip thereon.

Where it is especially desirable that the optical detection is performed at a controlled temperature, it is contemplated that the detector platform may further include a thermal control element (e.g., Peltier element, water heater/cooler, etc.) that heats or cools the platform, and with this the biochip. Such temperature control may be, for example, advantageously employed in differential hybridization where fluorescence of a label bound to a probe is quenched by a quencher located at the analyte. Dissociation of the analyte from the probe will then result in loss of quenching and increased fluorescence at the probe.

Therefore, particularly suitable platforms will include all elements that are operationally coupled to a stringency area and that are configured such that they can receive and retain (e.g., via a holding or guide mechanism, or by gravity where the platform is flat) a biochip, wherein the biochip is automatically moved from the stringency area to the detector platform.

In still further preferred aspects, the platform is coupled to an actuator that moves the platform along at least one, more preferably two, and most preferably three coordinates. In one especially preferred example, the actuator includes three stepping or piezo motors, wherein each of the motors controls movement of the platform along the x-coordinate, the y-coordinate, and the z-coordinate, respectively. There are numerous electrical actuators for platforms (e.g., microscopy platforms) known in the art, and all of such actuators are considered suitable for use herein. Furthermore, it is generally preferred that the actuator is controlled by a computer (preferably integral with the analyzer), wherein the computer receives and processes information from the detector, and wherein the information form the detector is used to move the platform via the actuator.

For example, in a typical operation of an analytic system, the computer may receive image information from the detector, wherein the image information includes an image of the platform with a biochip having three registration markers, and wherein the biochip is illuminated by the first light source. As in this example the registration markers exhibit fluorescence under illumination by the first light source and the excitation light from the first light source is filtered in the microscope, the image information will include three distinct signal areas corresponding to the three registration markers.

The computer will then execute an autofocus routine (e.g., by stepwise raising and/or lowering the platform, with each step acquiring an image of the biochip) in which the computer determines the best focal position for each of the registration markers. If the surface of the biochip is relatively even, the z-coordinate (focal height) for each of the three registration markers will be identical. On the other hand, if the surface of the biochip is relatively uneven, the z-coordinates of the three registration markers will be different, and the computer will then execute an algorithm that determines a focal plane having a tilt in at least one (e.g., where z-coordinate for first and second registration markers are identical) or two (e.g., where z-coordinate for all registration markers are not the same) directions.

Using the so determined surface geometry of the biochip, the computer will then assign a specific x-, y-, and z-coordinate for each of the analyte/probe spots by calculating the z-coordinate from the previously calculated surface geometry of the biochip and by calculating the x- and y-coordinate from a known spatial relationship between the registration markers and the analyte/probe spot. Consequently, it should be especially appreciated that the analytic system will require one, and ore typically two or three focusing routines to determine the correct focal position for a plurality of analyte/probe spots (e.g., up to 100 analyte spots, and even more). Such predictive focusing is especially advantageous where the microscope is a confocal microscope as confocal microscopy typically requires relatively high numeric apertures in the light collection path, and will therefore have significantly smaller depth of field (and with this much higher demand on correct focusing) than other optical methods. Moreover, as the first light source preferably provides a light with a wavelength that is substantially not absorbed (no more than 10%, more typically no more than 1%) by the label coupled to the probe and/or analyte, photobleaching and/or other photodeleterious effects from exposure to excitation light provided by the second and/or third light source are almost completely, if not entirely eliminated.

There are numerous methods and devices for autofocusing an electronic image known in the art, and all of such methods and devices are deemed suitable for use herein. For example, where an algorithm is run on the computer of the analytic system, commercial software is available for such purposes (e.g., Leica Microsystems Software Developer Kit). Alternatively, commercially available preconfigured systems may be employed (e g., Nikon E1000 Autofocus module).

Of course, it should further be recognized that various modifications to the inventive concept presented herein may be done. For example, it is contemplated that the relative movement of the platform to the detector and/or microscope may also be performed by moving the light path of the incident excitation light from the second and/or third light source via actuated mirrors or other light control elements. In another example, it should be recognized that the determination of the registration markers may be done at a first zoom aspect while (e.g., entire platform is visible in the detected field) while quantitative and/or qualitative analysis is performed at a second zoom aspect (e.g., only one probe/analyte spot is visible in the detected field). Therefore, in alternative aspects, it is contemplated that the platform may also be stationary with respect to the microscope.

With respect to data acquisition for qualitative and/or quantitative analysis, it is contemplated that all known methods (and especially those for fluorescence microscopy) are deemed suitable in conjunction with the teachings presented herein. For example, where sensitivity is especially important, it is contemplated that the image processing software acquires data from an area that is at least the area of the analyte/probe spot. On the other hand, where crosstalk between the analyte/probe spot and a neighboring analyte/probe spot should be avoided, only a portion (e.g., center portion, stripe, etc.) of the analyte/probe spot can be analyzed by the imaging software. There are numerous imaging software programs available and known in the art, and all of such programs are considered appropriate for use herein. Still further, it is contemplated that data acquisition may be enhanced using positive and/or negative control markers, which may be disposed on the chip in form of a probe spot, or which may be coupled to the probe (e.g., using a second fluorescent dye in a quantification assay, wherein the second dye is proportional to the amount of probe in the probe spot).

With respect to the computer, it is generally preferred that all functions, and especially autofocusing, control of fluidics management, automatic movement of the biochip in the analyzer, image analysis, and image data processing to provide a test result are performed on the same device using the same operating system. Therefore, particularly preferred computers will include commercially available Windows, Apple, Unix, or Linux-based systems with suitable interfaces to address the specific units in the analyzer. However, it is also contemplated that one or more functionalities in the analyzer may also be controlled separately. For example, an autofocus module may be operated separately from the image analysis, or the data processing to provide test data may be performed on a central computer that is coupled to numerous other analyzers.

In a particularly preferred aspect, a data transfer interface (e.g., telephonic or cable modem, DSL connector, or local/wide area network adapter) is electronically coupled to the detector (e.g., via the computer) and provides data to a computer that is in a remote location relative to the analytic device. For example, in one particularly contemplated aspect, a supplier or service contractor (typically in a location other than the entity where the analyzer in operated) electronically connects to the analytic device to service and/or troubleshoot the detector. Such service may include retrieving of error codes generated by the detector and/or computer, resetting one or more parameters, updating operating software for the detector (or other component), etc.

Figure 3:
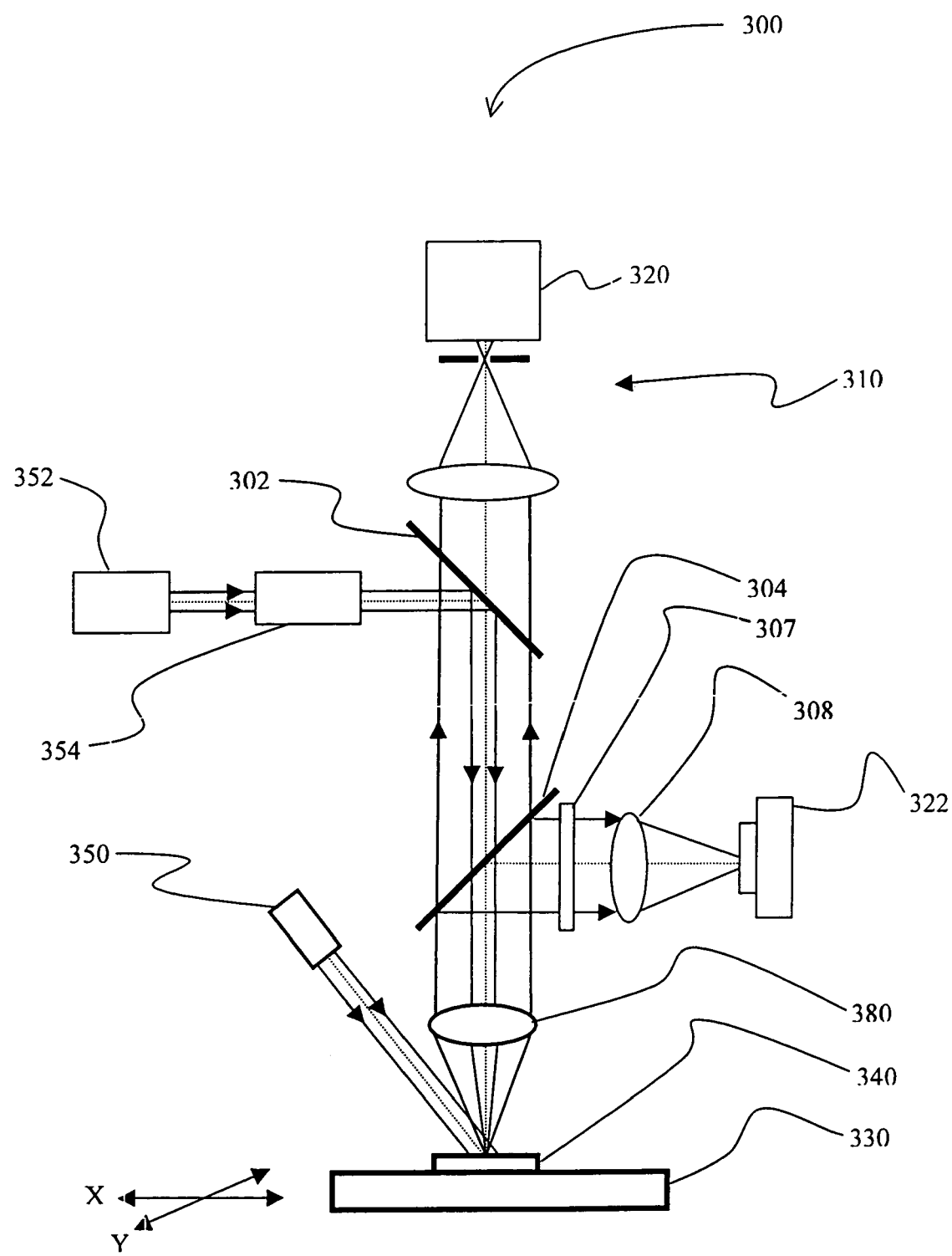
FIG. 3 is a schematic view of another exemplary detector configuration according to the inventive subject matter.

In an alternative preferred aspect of the inventive subject matter, as depicted in FIG. 3, an analytic system 300 includes a confocal microscope 310 that includes photomultiplier detector 320. Platform 330 receives and optionally retains biochip 340 which has a registration marker (not shown) and a plurality of optionally labeled probes/analytes (not shown) in predetermined positions (probe/analyte spots).

A first light source 350 illuminates the entire biochip (and more preferably even the entire platform) at a first angle relative to the surface of the platform 330 as schematically depicted by the arrows. The registration marker emits/reflects light in response to the illumination by the first light source as schematically indicated by the arrows pointing towards the CCD detector 322, and the emitted and/or reflected light is detected by the CCD detector 322 (after the emitted/reflected light is directed via dichroic mirror 304, optional filter 307, and lens or lens system 308). Electronically coupled to the CCD detector 322 is a computer (not shown) that executes an image analysis algorithm that determines the absolute position of the biochip on the platform and/or calculates the relative position of the registration marker and the sample/analyte spots on the biochip relative to the position of the light beam (from the second light source 352) that illuminates the labeled probe/analyte spots. Additionally or optionally, the computer may also execute an autofocus loop as described above to determine the proper z-coordinate for the biochip.

A second light source 352 (preferably one or more lasers with distinct wavelength maxima for the emitted light) provides a light beam that is passed through the telescope 354 to adjust the laser beam to a desired diameter (e.g., such that the laser beam is about 80 micrometer where the beam hits the biochip). The so adjusted laser beam is directed to the probe/analyte spot via dichroic mirrors 302 and 304. Reflected/emitted light from the label on the probe/analyte spot passes through objective lens (or lens system) 380, dichroic mirrors 302 and 304 to the PMT (photomultiplier tube) detector 320 of the confocal microscope 310.

It should further be particularly appreciated that in conventional microarray scanners, a biochip is continually scanned "pixel to pixel", or directly imaged on an image sensor. From this scan or image, a picture generated that identifies the fluorescence intensity on the biochip using specific software. While such systems may be especially advantageous for biochips with several hundreds or even thousands of probe/analyte spots, various disadvantages arise. For example, manual analysis is typically required to obtain signal intensity of the spots on the biochip, which may be a source for artificial errors. Furthermore, "pixel to pixel" scanning will generally require substantially more time than scanning "probe/analyte spot to probe/analyte spot". As molecular diagnostics of numerous typically involves less than 100 probe/analyte spots in one biochip, "probe/analyte spot to probe/analyte spot" scanning is generally more desirable. However, to realize such scanning in a time efficient manner, the proper coordinates of all spots on the chip must be identified, which is particularly difficult where the probe/analyte spots are relatively small and the biochip is automatically transferred from a sample processing platform to the detector.

Therefore, the inventors devised a system in which a biochip includes one or more (preferably three) registration spots (i.e., registration marker) in a predetermined location relative to the probe/analyte spots, wherein the probe/analyte spots have a predetermined location relative to each other. The registration spots can be either "black" spots, which absorb illuminating light without any or very weak reflection, or fluorescence spots, which excited and emitted spectra are far away from the dyes of the label on the probe/analyte. The absolute and/or relative location for the registration spots can be found automatically by a image analysis system. Based on simple geometric principles in which three spots determine a plane and in which the probe/analyte spots have a predetermined position relative to the registration spots, the space coordinates of all spots can be calculated.

In a further particularly preferred aspect, the inventor discovered that focusing along the z-coordinate (i.e., to achieve maximum clear outline and/or maximum sharp detail) may be entirely omitted where the numeric aperture of the objective lens is kept relatively small. In this context, it should be recognized that is generally preferred that an objective lens for fluorescence detection has a relatively high numeric aperture to efficiently collect light emitted from a label. However, relatively high numeric apertures generally require very short distances between the objective lens and the biochip (e.g., the working distance of an objective lens with a numeric aperture of more than 0.5 is less than about 4 mm). To enable automatic detection of a fluorescence signal without moving the biochip along the z-coordinate, the inventors used a objective lens with a numeric aperture of equal or less than 0.4. Especially preferred ranges for the numeric aperture of such objective lenses will lie between 0.2 to 0.4. Due to this fact, and the fact that the beam size of the first light source on microarray chip is relatively large (typically between about 20-100, and more typically between about 40-80 micrometer), the detecting optical system has relative long depth of focus (typically about 100 micrometer). Therefore, a biochip can be accurately read without moving the biochip along the z-coordinate to achieve maximum clear outline and/or maximum sharp detail.

Determination of the focal position along the x- and/or y-coordinate may be performed using a "white" registration spot (i.e., a registration spot that emits and/or reflects incident light) or a "black" registration spot (i.e., a registration spot that absorbs incident light). For example, where a "black" registration spot is employed, a section or the entire biochip is imaged on a CCD camera. In such configurations, a filter is generally is not necessary. After digital processing of the image, a computer program can find the location of the black registration spot on the image. Where desired, the biochip may then be moved along the x- and/or y-coordinate using predetermined steps, and further images are acquired to determine the location of a second or third black spot. Subsequently, a computer calculates the 2-dimensional coordinates of all probe/analyte spots based on the predetermined positions of the registration markers relative to the probe/analyte spots and the predetermined positions of the probe/analyte spots among each other.

Where "white" registration spots are used, it is generally preferred that the excitation and emission spectra of the white spots are distinct from those of the labels used with the probes/analytes to avoid undesired optical effects (e.g., cross talk or photobleaching). After the biochip (or portion thereof) is illuminated by a light source the objective lens collects reflection light and fluorescence of a registration spot. A dichroic mirror directs the light to a filter that blocks the reflected light of the light source and allows passage of the fluorescence registration from the registration marker to the CCD detector. As already discussed above, the CCD detector will then produce an image that is analyzed for the registration marker signal for proper determination of the focal position. With respect to the first and second light sources, the detectors, and other components for analytical systems of FIG. 3, the same considerations as described above apply.

Therefore, it should be especially appreciated that in contemplated analytic devices a first optical subsystem may be employed to determine the focal position of the biochip (in at least two spatial coordinates, and more typically in all three spatial coordinates) using a first light source, while a second optical subsystem may be employed to determine the presence and/or quantity of an analyte that is bound to the biochip using a second light source.

Therefore, and viewed from one perspective, the inventors contemplate an analytic system for optical detection of a plurality of analytes that are bound to a biochip, wherein the system includes a platform coupled to a detector and movable along an x-coordinate, a y-coordinate, and a z-coordinate relative to the detector, and wherein the platform is configured to receive a biochip. Particularly preferred biochips have a registration marker and a plurality of analytes in predetermined positions relative to the registration marker. A first light source illuminates the registration marker to generate a registration marker signal, and a second light source illuminates at least one of the plurality of analytes to generate an analyte signal, wherein the focal position for detection of the analyte signal by the detector is determined by the analytic system using the registration marker signal.

Viewed from another perspective, the inventors contemplate an analytic system for micro-optical analysis of a biochip having a first light source and a second light source, wherein the first light source illuminates a registration marker on the biochip to provide a registration marker signal, wherein the second light source illuminates an analyte to provide an analyte signal, and wherein a focal position for detection of the analyte signal with a confocal microscope is determined using the registration marker signal. In such systems, it is generally contemplated that the analyte signal has a round or elliptic shape with a diameter of no more than 500 micrometer, more typically no more than 300 micrometer, and most typically no more than 100 micrometer. Depending on the particular size and shape of the analyte signal (typically provided by the analyte spot), a test result is calculated from an average signal value of a portion of the round shape, or of the entire analyte spot.

It is still further contemplated that such systems may further comprise a third light source illuminating the analyte to generate a second analyte signal, wherein a test result is calculated using the analyte signal and the second analyte signal. Typically in such systems, the first light source is a laser or a light emitting diode, and wherein the second light source is a laser, while the registration marker and the analyte are illuminated at a different angle by the first and the second light source, respectively. However, alternative configurations as described above may also apply for such systems.

Additionally or optionally, suitable analytic devices may further include a multi-reagent pack, a sample processing platform, and/or an automated pipettor to form an integrated analytic device. Particularly preferred multi-reagent packs contemplated in conjunction with the teachings presented herein include those described in our co-pending international patent application with the title "Multi-Reagent Pack", filed May, 28, 2003, which is incorporated by reference herein. Particularly preferred sample processing platforms contemplated in conjunction with the teachings presented herein include those described in our co-pending international patent application with the title "Integrated Sample Processing Platform", filed May, 28, 2003, which is incorporated by reference herein. Particularly preferred automatic pipettors contemplated in conjunction with the teachings presented herein include those described in our co-pending international patent application with the title "Level-Controlled Pipette For Automated Analytic Devices", filed May 28, 2003, which is incorporated by reference herein.

Thus, specific embodiments and applications of improved detector configurations have been disclosed. It should be apparent, however, to those skilled in the art that many more modifications besides those already described are possible without departing from the inventive concepts herein. The inventive subject matter, therefore, is not to be restricted except in the spirit of the appended claims. Moreover in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. An analytic system for optical detection of a plurality of analytes that are bound to a biochip, the analytic system comprising:
   a platform functionally coupled to a confocal microscope detector and movable along an x-coordinate, a y-coordinate, and optionally a z-coordinate relative to the detector, wherein the platform is configured to receive a biochip;
   wherein the biochip has a plurality of registration markers and further has a plurality of analytes in predetermined positions relative to the registration markers;
   a first light source that is configured to illuminate the registration markers at a first angle relative to the z-coordinate to generate registration marker signals, and further comprising a second light source that is configured to sequentially illuminate at least two of the plurality of analytes at a second angle relative to the z-coordinate to generate at least two individual analyte signals, respectively;
   a computer configured to determine the position of the biochip with respect to a given x-coordinate value and a given y-coordinate value using the registration marker signals; and
   wherein the first and the second angles are different.

2. The analytic system of claim 1 wherein the detector comprises an objective lens or an objective lens system with a numeric aperture that is sufficient to allow detection of the analyte signal without moving the platform along the z-coordinate.

3. The analytic system of claim 1 wherein the first light source has a wavelength maximum that is different from an absorption maximum of an optically detectable label of the at least one of the plurality of analytes.

4. The analytic system of claim 1 further comprising a third light source that illuminates the at least one of the plurality of analytes or another one of the plurality of analytes to generate a second analyte signal, and wherein the third light source has a wavelength maximum that is different from both, the wavelength maximum of the first light source and the absorption maximum of an optically detectable label of the at least one of the plurality of analytes or another one of the plurality of analytes.

5. The analytic system of claim 1 wherein the registration marker and the at least one of the analytes are illuminated at a different angle and a different wavelength by the first and the second light source, respectively.

6. The analytic system of claim 1 wherein the first light source is a laser or a light emitting diode, and wherein the second light source is a laser.

7. The analytic system of claim 1 wherein the registration marker comprises a fluorescent dye, a luminescent compound, a phosphorescent compound, or a reflective compound.

8. The analytic system of claim 1 wherein the analyte signal is a fluorescence signal, a chemiluminescence signal, or a phosphorescence signal.

9. The analytic system of claim 1 wherein the detector comprises a photo-multiplier tube or a charge-coupled device.

10. The analytic system of claim 1 further comprising a second and a third registration marker, and wherein a vertical focal position for detection of the analyte signals by the detector is determined by the analytic system using registration marker signals from the registration marker, the second registration marker and the third registration marker.

11. The analytic system of claim 1 wherein the analyte signal is normalized by the analytic system using a positive control marker on the biochip.

12. The analytic system of claim 1 further comprising a data transfer interface electronically coupled to the detector.

13. The analytic system of claim 12 wherein the data transfer interface is informationally coupled to a computer in a remote location.

* * * * *